United States Patent
Bouvier et al.

(10) Patent No.: US 10,413,846 B2
(45) Date of Patent: Sep. 17, 2019

(54) TECHNIQUES FOR THERMALLY INSULATING A LIQUID CHROMATOGRAPHIC COLUMN

(71) Applicant: Waters Technologies Corporation, Milford, MA (US)

(72) Inventors: Edouard S.P. Bouvier, Stow, MA (US); Pamela C. Iraneta, Brighton, MA (US); Joseph A. Luongo, Walpole, MA (US); Joseph A. Jarrell, Newton Highlands, MA (US)

(73) Assignee: Waters Technologies Corporation, Milford, MA (US)

( * ) Notice: Subject to any disclaimer, the term of this patent is extended or adjusted under 35 U.S.C. 154(b) by 541 days.

(21) Appl. No.: 14/406,279

(22) PCT Filed: Jun. 26, 2013

(86) PCT No.: PCT/US2013/047800
§ 371 (c)(1),
(2) Date: Dec. 8, 2014

(87) PCT Pub. No.: WO2014/008058
PCT Pub. Date: Jan. 9, 2014

(65) Prior Publication Data
US 2015/0129474 A1  May 14, 2015

Related U.S. Application Data

(60) Provisional application No. 61/668,560, filed on Jul. 6, 2012.

(51) Int. Cl.
*B01D 15/16* (2006.01)
*B01D 15/20* (2006.01)
(Continued)

(52) U.S. Cl.
CPC ........... *B01D 15/22* (2013.01); *B01D 15/161* (2013.01); *B01D 15/20* (2013.01); *G01N 30/30* (2013.01);
(Continued)

(58) Field of Classification Search
CPC ...... B01D 15/22; B01D 15/161; B01D 15/20; G01N 30/30; G01N 30/54; G01N 30/88;
(Continued)

(56) References Cited

U.S. PATENT DOCUMENTS

| 3,732,982 A | 5/1973 | Dunnill et al. |
| 4,427,123 A | 1/1984 | Komeda et al. |

(Continued)

FOREIGN PATENT DOCUMENTS

| EP | 0305817 A2 | 3/1989 |
| GB | 1059169 A | 2/1967 |

(Continued)

OTHER PUBLICATIONS

Poling., B., et al., "The Properties of Gases and Liquids". New York: McGraw-Hill. p. 10.18. (2001).*

(Continued)

*Primary Examiner* — Benjamin L Lebron

(57) ABSTRACT

An apparatus for performing liquid chromatography includes a chromatography column, and an insulating member surrounding the chromatography column wherein the insulating member is formed from a vacuum chamber surrounding the chromatography column. Another apparatus for performing liquid chromatography includes a chromatography column, and an insulating member surrounding the chromatography column, wherein the insulating member includes aerogel. Also described is a method of insulating a chromatography column comprising forming a jacket surrounding the chromatography column, and creating a (Continued)

vacuum chamber in an area between the jacket and the chromatography column.

20 Claims, 11 Drawing Sheets

(51) Int. Cl.
| | |
|---|---|
| B01D 15/22 | (2006.01) |
| G01N 30/30 | (2006.01) |
| G01N 30/54 | (2006.01) |
| G01N 30/88 | (2006.01) |
| G01N 30/02 | (2006.01) |

(52) U.S. Cl.
CPC .............. *G01N 30/54* (2013.01); *G01N 30/88* (2013.01); *G01N 2030/027* (2013.01); *G01N 2030/3007* (2013.01); *G01N 2030/3015* (2013.01); *G01N 2030/3038* (2013.01); *G01N 2030/3046* (2013.01); *G01N 2030/3061* (2013.01); *G01N 2030/3084* (2013.01); *G01N 2030/889* (2013.01); *Y10T 29/49826* (2015.01)

(58) Field of Classification Search
CPC ....... G01N 2030/30; G01N 2030/3007; G01N 2030/3015; G01N 2030/3023; G01N 2030/303; G01N 2030/3038; G01N 2030/3046; G01N 2030/3053; G01N 2030/3061; G01N 2030/3069; G01N 2030/3076; G01N 2030/3084; G01N 2030/3092; G01N 2030/027; G01N 2030/889; C08J 5/005; C08J 2383/04; C08J 9/143; C08J 9/40; C08J 2375/04; Y10T 29/49826

See application file for complete search history.

(56) References Cited

U.S. PATENT DOCUMENTS

| | | | | |
|---|---|---|---|---|
| 4,732,581 | A * | 3/1988 | Cheh | B01D 59/24 95/87 |
| 4,780,116 | A * | 10/1988 | Cheh | B01D 53/025 96/102 |
| 4,997,124 | A | 3/1991 | Kitabatake et al. | |
| 5,638,896 | A | 6/1997 | Nishino et al. | |
| 5,851,458 | A * | 12/1998 | De Vos | B29C 44/5609 264/46.5 |
| 5,965,231 | A * | 10/1999 | Rotermund | C08J 9/127 252/372 |
| 5,983,710 | A * | 11/1999 | Uhen | G01N 30/30 73/23.25 |
| 6,029,498 | A | 2/2000 | Walters et al. | |
| 6,157,015 | A | 12/2000 | Gaisford et al. | |
| 6,217,829 | B1 * | 4/2001 | Mustacich | G01N 30/30 422/70 |
| 6,666,074 | B2 * | 12/2003 | Gerner | G01N 30/30 73/61.52 |
| 7,374,063 | B2 | 5/2008 | Reid | |
| 7,681,299 | B2 | 3/2010 | Reid | |
| 2006/0054558 | A1 * | 3/2006 | Jones | B01D 15/161 210/656 |
| 2007/0175270 | A1 * | 8/2007 | Lunsford | G01N 30/30 73/61.55 |
| 2008/0020154 | A1 * | 1/2008 | Landon | B82Y 30/00 428/34 |
| 2008/0216823 | A1 | 9/2008 | Kmetovicz et al. | |
| 2009/0189015 | A1 | 7/2009 | Alavi | |
| 2010/0162801 | A1 | 7/2010 | Hayashi et al. | |
| 2010/0227764 | A1 | 9/2010 | Willén et al. | |
| 2011/0120031 | A1 | 5/2011 | Scherba | |
| 2011/0214770 | A1 | 9/2011 | Knitt | |
| 2011/0264084 | A1 | 10/2011 | Reid | |
| 2012/0011921 | A1 * | 1/2012 | Broeckhoven | B01D 15/161 73/61.53 |
| 2014/0090737 | A1 | 4/2014 | Reid | |
| 2016/0084425 | A1 | 3/2016 | Reid | |

FOREIGN PATENT DOCUMENTS

| | | |
|---|---|---|
| WO | 2007/059494 A2 | 5/2007 |
| WO | 2014/008058 A1 | 1/2014 |

OTHER PUBLICATIONS

Pavia, D.L., Lampman, G.M., Kriz, G.S., Engel, R.G., (2005). Introduction to organic laboratory techniques: a small scale approach; Technique 15: Fractional distillation, azeotropes. Unites States: Thomson Brooks/Cole. Title, pp. 744 and 754. (Year: 2005).*
Pavia, D.L., Lampman, G.M., Kriz, G.S., Engel, R.G., (2005). Introduction to organic laboratory techniques: a small scale approach; Technique 15: Fractional distillation, azeotropes. United States: Thomson Brooks/Cole. pp. 744-764.*
K. Broeckhoven, et al., "Towards a solution for viscous heating in ultra-high pressure liquid chromatography using intermediate cooling," Journal of Chromatography A, 1217 (2010) 2022-2031.
Joanna Kostka, et al., "Modeling of thermal processes in very high pressure liquid chromatography for column immersed in a water bath: Application of the selected models," Journal of Chromatography A, 1217 (2010) 4704-4712.
Fabrice Gritti, et al, "Optimization of the thermal environment of columns packed with very fine particles," 1216 (2009) 1353-1362.
Fabrice Gritti, et al., Achieving quasi-adiabatic thermal environment to maximize resolution power in very high-pressure liquid chromatography, Theory, models, and experiments, Supplementary Material, Waters Corporation, Mar. 28, 2016.
Fabrice Gritti, et al., Achieving quasi-adiabatic thermal environment to maximize resolution power in very high-pressure liquid chromatography, Theory, models, and experiments, Journal of Chromatography A, 1444, Mar. 28, 2016, 86-98.
Fabrice Gritti, "Measurement of the axial and radial temperature profiles of a chromatographic column Influence of thermal insulation on column efficiency," Science Diet, Journal of Chromatography A, 1138 (2007) 141-157.
Fabrice Gritti, "Consequences of the radial heterogeneity of the col. temperature at high mobile phase velocity," Science Diet, Journal of Chromatography A, 1166 (2007) 47-60.
Fabrice Gritti,"Influence of Viscous Friction Heating on the Efficiency of Columns Operated under Very High Pressures," Analytical Chemistry, May 1, 2009, vol. 81, No. 9, 3365-3384.
Fabrice Gritti,"Complete Temperature Profiles in Ultra-High-Pressure Liquid Chromatography Columns," Analytical Chemistry, Jul. 1, 2008, vol. 80, No. 13, 5009-5020.
Fabrice Gritti, et al., Optimization of the thermal environment of columns packed with very fine particles, Journal of Chromatography A, 1216 (2009) 1353-1362.
International Search Report dated Nov. 27, 2013.
International Preliminary Report on Patentability dated Jan. 15, 2015.
https://youtube.com/watch?v=CVDrz0Xghm0, Oct. 27, 2014, Youtube video, SureUP vacuum flask production process.
https://www.youtube.com/watch?v=mThNcqpko7s, Jun. 6, 2013, Youtube video, Vacuum Thermos Factory, 3 pages/image.
International Search Report and Written Opinion for International Application No. PCT/US2017/027576 dated Oct. 18, 2017.
International Preliminary Report on Patentability for International Application No. PCT/US20171027576 dated Oct. 25, 2018.

* cited by examiner

TECHNIQUES FOR THERMALLY INSULATING A LIQUID CHROMATOGRAPHIC COLUMN

RELATED APPLICATION

This application claims priority to and the benefit of U.S. provisional application No. 61/668,560, filed Jul. 6, 2012, entitled TECHNIQUES FOR THERMALLY INSULATING A LIQUID CHROMATOGRAPHIC COLUMN, which is incorporated by reference herein.

TECHNICAL FIELD

This application generally relates to techniques for use with liquid chromatography, and more particularly to thermally insulating a liquid chromatography column.

BACKGROUND INFORMATION

Chromatography is a technique for separating compounds, such as those held in solution, where the compounds will exhibit different affinity for a separation medium in contact with the solution. As the solution flows through such an immobile separation medium, the compounds separate from one another. Common chromatographic separation instruments include liquid chromatography (LC) systems. Such LC systems are known and used for analyzing sample solutions that may include different chemical compounds. LC systems may operate at high pressures such as at 5,000 PSI and greater. A typical LC system includes a pump for pumping a liquid solution, an injector for injecting the sample into the liquid fluid stream, a chromatography column packed with packing material used as the separation medium and tubing for carrying the sample solution and liquid fluid from the injector to the chromatography column. The tubing may then be used to further transport the sample solution output from the LC column to a detector for analyzing the sample solution. The detector may be any suitable detector such as a mass spectrometer, a UV absorbance detector, an evaporative light scattering detector, and the like.

During operation of the LC system, a liquid solvent is pumped into the LC system at high pressure. The injector may be used to inject controlled volumes of a sample, either manually or automatically, into the system where the sample is carried with the liquid solvent in a fluid stream to the packed LC column where the sample may then be separated. Because each of the chemical compounds in the sample solution react in a different manner with the LC column packing material, the various chemical compounds flow through the packed LC column at different rates. The different chemical compounds in the sample solution separate from each other as the sample solution flows through the column. The separated chemical compounds as output from the LC column proceed to the detector where they may be further analyzed, for example, to determine physical characteristics of the compounds for purposes of identification and/or quantification.

SUMMARY OF THE INVENTION

In accordance with one aspect of the invention is an apparatus for performing liquid chromatography comprising: a chromatography column; and an insulating member surrounding the chromatography column wherein the insulating member is formed from a vacuum chamber surrounding the chromatography column. The vacuum chamber may comprise an inert gas. The inert gas may be any of argon, krypton, xenon, carbon dioxide and sulfur hexafluoride. The vacuum chamber may comprise atmospheric gas. The chromatography column and the insulating member may be integrated into a single component forming an insulated chromatography column. The apparatus may also comprise a jacket surrounding the chromatography column, wherein the vacuum chamber is formed in an area between the chromatography column and the jacket. The jacket may be made of steel. The jacket may be an outer layer of a housing of a column heater. The vacuum chamber forming the insulating member may provide thermal insulation for the chromatographic column. The insulating member may substantially prevent a radial thermal gradient from forming within the chromatographic column. The apparatus may also include a heater that heats a mobile phase prior to an inlet of the chromatographic column. The heater and the chromatographic column may be included in a column heater and the vacuum chamber may be formed in an area between the chromatographic column and an outer wall of the column heater. The thermal conductivity of the inert gas may be about or less than 0.02 W/mK. The vacuum chamber may be at a pressure of about $10^{-3}$ atm or less.

In accordance with another aspect of the invention is an apparatus for performing liquid chromatography comprising: a chromatography column; and an insulating member surrounding the chromatography column, wherein the insulating member includes aerogel. The insulating member may be formed from a chamber surrounding the chromatography column. The chamber may include granular aerogel particles. The chamber may be at ambient pressure. The chamber may be a vacuum chamber at a pressure less than ambient pressure. The insulating member may be a molded component including aerogel.

In accordance with another aspect of the invention is a method of insulating a chromatography column comprising: forming a jacket surrounding the chromatography column; and creating a vacuum chamber in an area between the jacket and the chromatography column. The vacuum chamber may include atmospheric gas. The vacuum chamber may include an inert gas having a thermal conductivity of about or less than 0.02 W/mK. The inert gas may be any of argon, krypton, xenon carbon dioxide and sulfur hexafluoride. A vacuum pump may be connected to a through hole in the jacket and may be used to reduce pressure in the area to below an atmospheric pressure thereby creating a vacuum in the area. The method may include sealing the through hole thereby forming an airtight seal.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
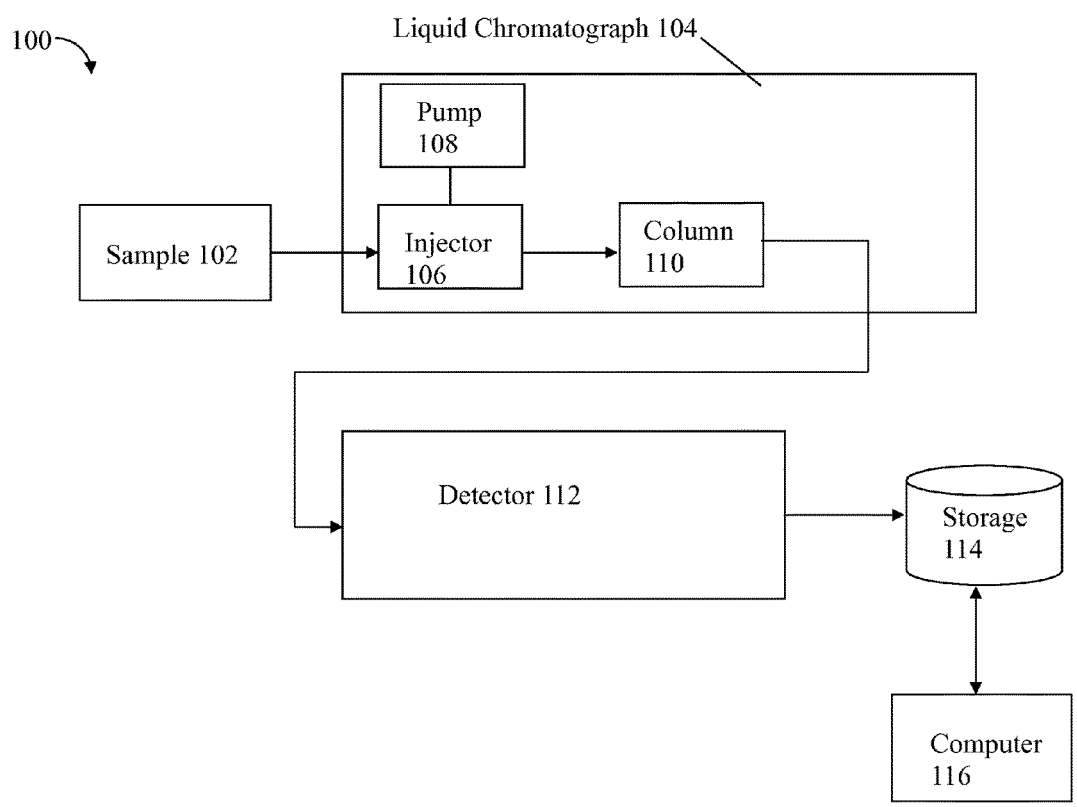
FIG. 1 is an example of a system that may utilize the chromatographic column embodiments described in accordance with techniques herein.

Referring to FIG. 1, shown is an embodiment of a system in accordance with techniques herein. The system 100 may include components such as analytical instruments for performing sample analysis. In one embodiment, the system 100 may be an LC instrument system including a liquid chromatograph (LC) 104, detector 112, storage 114, and computer 116. As will be described in following paragraphs, the system 100 may be used to perform analysis of sample 102 for detecting one or more compounds of interest. The LC 104 may include an injector 106 that receives sample 102, a pump 108, and a column 110. The liquid sample 102 may be introduced as an input to the LC 104. Although not illustrated in FIG. 1, the LC 104 may also include an optional column heater. As described in more detail below, the computer 116 may be used to control operation of the components and used in connection with data acquisition to store analysis data to storage 114. As also described in more detail below, the sample and mobile phase traverse through the fluidic path of the system.

In operation, the sample 102 is injected into the LC 104 via the injector 106. The pump 108 pumps the sample through the column 110 to separate the sample into component parts according to retention time through the column 110. A high pressure stream of chromatographic solvent provided by pump 108 and injector 106 forces sample 102 to migrate through a chromatographic column 110 in the LC 104. Column 110 typically comprises a packed column of porous, non-porous or superficially-porous particles, made of silica, polymer, or an organohybrid silica whose surface may be chemically modified. The output from the column 110 is input to the detector for analysis. The detector 112 may be any suitable detector such as a UV absorbance detector, an evaporative light scattering detector, a mass spectrometer, and the like.

In one embodiment, the LC system may be, for example, a High Performance Liquid Chromatography (HPLC) or an Ultra Performance Liquid Chromatography (UPLC) system such as the ACQUITY UPLC® and nanoACQUITY UPLC® systems from Waters Corporation of Milford Mass. An LC system such as the foregoing from Waters Corporation may operate under high pressure such as in the range of 5000 PSI (e.g, exemplary for some HPLC systems) to 15000 PSI (exemplary for some UPLC systems).

A control means (not shown) provides control signals for the various power supplies (not shown) which respectively provide the necessary operating potentials for the components of the system 100 such as the 104 and 112. These control signals determine the operating parameters of the instrument. The control means is typically controlled by signals from a computer or processor, such as the computer 116.

The storage 114 may be any one or more different types of computer storage media and/or devices. As will be appreciated by those skilled in the art, the storage 114 may be any type of computer-readable medium having any one of a variety of different forms including volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, (DVD) or other optical storage, magnetic cassettes, magnetic tape, magnetic disk storage or other magnetic storage devices, or any other medium which can be used to store the desired code, data, and the like, which can accessed by a computer processor.

The computer 116 may be any commercially available or proprietary computer system, processor board, ASIC (application specific integrated circuit), or other component which includes a processor configured to execute code stored on a computer readable medium. The processor, when executing the code, may cause the computer system 116 to perform processing steps such as to access and analyze the data stored on storage 114. The computer system, processor board, and the like, may be more generally referred to as a computing device. The computing device may also include, or otherwise be configured to access, a computer readable medium, such as represented by 114, comprising executable code stored thereon which cause a computer processor to perform processing steps.

One or more molecular species migrates through column 110 and each emerges, or elutes, from column 110 and is detected by detector 112. The time that it takes for a molecule to traverse through the column is commonly is referred to as the molecule's retention time. That is, a molecule that elutes from a column at retention time t in reality elutes over a period of time that is essentially centered at time t. The elution profile over the time period is referred to as a chromatographic peak whereby the retention time for the molecule corresponds to the apex of the profile. The elution profile of a typically well-behaved chromatographic peak can be described by a Normal (Gaussian) distribution. The peak has a width that typically is described by its full width at half height, or half-maximum (FWHM).

The retention time and chromatographic peak profile of a molecule eluting from a chromatographic support matrix (e.g., such packing material of column 110 or other separation medium for separating chemical compounds of a sample solution) is a function of the physical and chemical interaction of that molecule between the support matrix and mobile phase. The degree of interaction that a molecule has between the support matrix and the mobile phase dictates the chromatographic profile and retention time for that molecule. In a complex mixture, each molecule is chemically different. As a result, each molecule can have a different affinity for the chromatographic matrix and the mobile phase. Consequently, each can exhibit a unique chromatographic profile.

When the sample solution flows through the packed LC column at high pressures, frictional heat is generated within the column. The amount of frictional heat generated is a function of several factors such as, for example, the flow rate of the mobile phase, the particle size of the column packing material, and the dimensions (length and inner diameter) of the column. Such frictional heat may result in an increase or difference in the temperature at the center of the column relative to the outer edges or walls of the column thereby causing a radial thermal gradient which adversely affects the performance of the LC system. As known in the art, LC performance may be measured, for example, in terms of efficiency by plate count, reduced plate height, and/or tailing factors. Adversely affecting LC performance may be observed, for example, by having a wider than normal/expected peak width, asymmetrical peak shape, reduced plate count, and the like. For example, the radial thermal gradient, where the temperature at the column center is greater than at the column outer edges, causes the liquid mobile phase passing through the center to have a lower viscosity than at the outer edges. As a result, the liquid mobile phase flows faster through the column center than at the outer edges. Also, since chromatographic retention typically decreases as temperature increases, an analyte migrates faster at the center of the column. To further illustrate, for example, chromatographic peaks may be broader or wider due to such changes in viscosity (and thus flow rate) due to radial thermal gradients in the column as just described. Such increased peak widths may result in overlapping peaks thereby adversely affecting the quality of the information obtained from LC data. Therefore, due to such adverse effects (the foregoing of which is one example), it is desirable to minimize or reduce radial thermal gradients to improve LC performance.

Additionally, such frictional heat may cause a temperature difference with respect to the direction of flow (also referred to as the axial direction with respect to the axis of directional flow) through the LC column. Such a temperature difference in the axial direction may be referred to as an axial thermal gradient and may be measured by determining a temperature $T_{in}$ of the liquid mobile phase entering into the LC column and a temperature $T_{out}$ when exiting the LC column. When the particle size of packing in the LC column is, for example, a 5 micron particle, there may be little difference between $T_{in}$ and $T_{out}$ in the axial direction (e.g., may be 1 or 2 degrees C.). However, with smaller size particles comprising the LC column packing such as particles having a size of 1.7 microns, the difference between $T_{in}$ and $T_{out}$ in the axial direction is much larger in comparison to the axial thermal gradient for the 5 micron size particle case. The axial thermal gradient may affect retention but may have a minimal or insignificant adverse impact on LC performance.

Generally, any type of temperature gradients with respect to the LC column, (e.g., including any of radial and axial thermal gradients), may have an effect upon mobile phase viscosity, the speed or rate at which an analyte in mobile phase diffuses, and may also affect retentivity (e.g., how an analyte interacts with the surfaces of the particles in the column packing) thereby affecting chromatographic retention time. As noted above, an axial thermal gradient generally does not have a significant negative or adverse affect on chromatographic performance. However, existence of a radial thermal gradient typically does have a significant adverse impact on LC performance such as may be measured in terms of column efficiency.

Through modeling and general testing of column environments including adiabatic, isothermal and ambient, it has been determined that having a column environment of adiabatic (or that which approaches adiabatic conditions as close as possible) is best in efforts to have the smallest or minimal radial thermal gradient and the highest column efficiency (e.g., such as may be measured in terms of USP Plate Counts and/or HETP (Height Equivalent to the Theoretical Plate). Isothermal may be defined as having a constant column temperature at the column outer wall such as, for example, by placing the column in a water bath. Adiabatic may be defined as providing an outer insulation to the column to thereby reduce or eliminate any addition or removal or heat from the column. Ambient may be defined as having the column in still air.

To this end, described herein are embodiments on the LC column which provide for such adiabatic conditions and minimize radial thermal gradients to maximize column efficiency and performance. During operation of the LC system with such a column as described herein with the goal of providing adiabatic conditions, the column heats up naturally via friction as described elsewhere herein. At some point, the column and LC system will reach a steady state temperature. Such a steady state with respect to column temperature may be determined by having $T_{in}$, $T_{out}$, and the difference therebetween (e.g., axial temperature gradient) be relatively or substantially constant. In this steady state with respect to column temperature (as may be determined by obtaining substantially constant values for $T_{in}$, $T_{out}$ and the axial thermal gradient and with adiabatic conditions using the insulated column described herein), the temperature at the column outer wall and at the column center will be substantially the same thereby minimizing or eliminating the radial thermal gradient. Therefore, in such a steady state temperature using the column embodiments described in more detail herein providing adiabatic conditions via column insulation, there will be an axial thermal gradient and minimal radial thermal gradient.

It will be appreciated by those of ordinary skill in the art that the LC system may reach steady state prior to injecting a sample in connection with performing an LC experiment.

Figure 2:
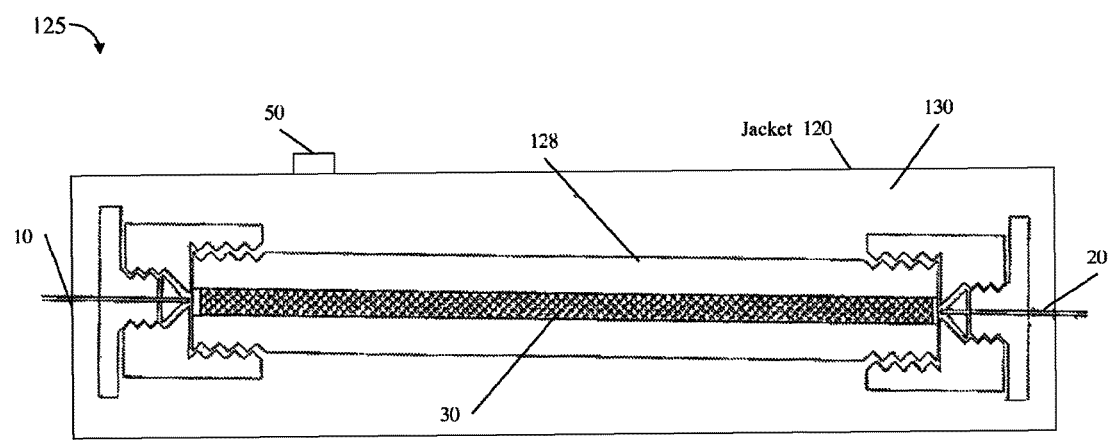
FIGS. 2-4 and 8-10 are examples of various chromatographic column embodiments in accordance with techniques herein.

Referring to FIG. 2, shown is an example of an embodiment of a chromatography column in accordance with techniques herein. The embodiment of FIG. 2 may be used as the column 110 in the system of FIG. 1. FIG. 2 illustrates a side cutaway view of a high performance liquid chromatography (HPLC) column 128 within an insulating layer or member 130 formed between the column 128 and an outer jacket 120. Inlet tube 10 carries sample solution into the HPLC column 128 and outlet tube 20 carries sample solution out of the HPLC column 128. Element 30 represents the chromatographic separation medium, such as beads or other column packing material. The insulating layer or member 130 may provide thermal insulation for the HPLC column capable of operating at pressures in excess of 5,000 PSI. In the embodiment of 125, the insulation layer or member 130 may be a vacuum chamber acting as a thermal insulator and having a pressure that is below local atmospheric pressure (e.g., below the atmospheric pressure external to the area 120 or surrounding the jacket 120). Examples of more specific pressure(s) that may be used in an embodiment in connection with the vacuum within the area 130 surrounding the column are provided elsewhere herein. As illustrated, the column 128 may be placed within jacket 120 having suitable airtight sealing to isolate the column 128 (along with other illustrated components attached thereto) located within the jacket 120 from the environment outside the jacket 120. Once the column 128 is placed within the jacket 120, a vacuum may be created in space or chamber 130 by pumping out the air therein surrounding the column 128 within the jacket. The air may be pumped out by connecting a vacuum pump (not illustrated) to through hole 50 of the jacket 120. Once the air has been evacuated from the space 130, the through hole 50 may be sealed off thereby creating a vacuum chamber or space represented by 130 in the area surrounding the column 128 within the jacket 120.

As a first alternative to the foregoing in which a vacuum chamber is created in space 130, the air in space 130 may be displaced with a heavy inert gas such as argon, krypton or xenon. In such an embodiment, a source of the inert gas (not illustrated) may be connected to through hole 50 to displace the atmospheric gas of space 130 with the inert gas. The through hole 50 may then be closed off using any suitable means as described above to form an air tight seal. In this first alternative, the insulating layer 130 may be formed by the inert gas located therein. As yet a further variation to the above prior to closing off through hole 50, once the inert gas is provided in space 130, a vacuum pump may then be attached to through hole 50 to create a vacuum by pumping out the inert gas. Once a sufficient vacuum has been created, the through hole 50 may then be closed off as described above to form a suitable air tight seal.

Thus, based on the foregoing exemplary alternatives, an embodiment may form the insulating layer surrounding the column by pumping out the air or atmospheric gas in the space surrounding the column thereby creating a vacuum chamber (with minimal atmospheric gas) as the insulating layer 130. An embodiment may also form the insulating layer surrounding the column by replacing the air or atmospheric gas in the space surrounding the column with an inert gas thereby creating an inert gas chamber or layer as the insulating layer 130 which is at atmospheric pressure. An embodiment may also form the insulating layer surrounding the column by displacing the air or atmospheric gas in the space surrounding the column with an inert gas and then pumping out the inert gas in the space surrounding the column thereby creating a vacuum chamber (with minimal inert gas) as the insulating layer 130.

In connection with the vacuum that may be formed in the chamber of the insulating layer 130, it should be noted that a true vacuum has the lowest thermal conductivity whereby heat can only be transported by radiative heating. At very low pressure (e.g., approximately less than $10^{-3}$ atm), thermal conductivity is directly proportional to pressure. This region is also known in the art as the Knudsen domain, where the mean free path of the molecules is large compared to the dimensions of the chamber. At low pressures such as, for example, in the approximate range of $10^{-3}$ atm to 10 atm, thermal conductivity is a very weak function of pressure, increasing less than ~1% per bar. Thus, some embodiments may utilize a vacuum having a preferred pressure of approximately equal to, or less than, $10^{-3}$ atm. Other embodiments using techniques herein may utilize other pressures such as in the approximate range of $10^{-3}$ atm to 10 atm although pressures of approximately $10^{-3}$ atm or less may be preferred.

With respect to the gas that may be used in connection with 130 in embodiments described herein such as in the vacuum chamber at one of the pressures described herein, it should be noted that heavy gases provide better thermal insulation than lighter gases, as they have lower thermal conductivity. Thermal conductivity in general decreases as molecular weight increases. An embodiment may use, for example, argon, xenon, and/or krypton which are much heavier than air, and thus have lower thermal conductivity. As another example, an embodiment may form insulating layer 130 using a gas including sulfur hexafluoride.

It should be noted that the column inner diameter may be any suitable dimension, such as 1 mm (millimeter) or greater although the increased benefits from using such a column may be more apparent as the column inner diameter increases (e.g., for example at inner column diameters of 2 mm and greater). An embodiment may also use columns having any particle size for the packing material or, more generally, separation medium. However, columns using smaller particle sizes, (e.g., such as particles having a size of 2.5 microns or smaller) may typically obtain greater benefits because more frictional heat is generated thereby resulting in larger thermal gradients. The outer column wall of column 128 may be made from steel, titanium, or other suitable material able to withstand the HPLC operating pressures such as generally in excess of 5,000 PSI. The surrounding jacket 120 may be made from steel or other suitable material into which a through hole 50 may be machined or otherwise formed. The through hole 50 may be sealed in any suitable manner, such as by crimping, capping (e.g., using a removable or permanent cap), and the like, to thereby providing an airtight seal for use in creating the vacuum in space represented by 130. For example, the through hole 50 may be sealed by having a removable cap (e.g. via threading) applied thereto.

In one embodiment, the area 130 may form an insulating layer or member and provide sufficient insulation preventing thermal conductivity between the column 128 and ambient temperature such as of the environment outside of or surrounding the jacket 120. The area denoted as 130 forming the insulating layer or member may provide thermal conductivity, for example, that is approximately at or below 0.02 W/mK. It should be noted that ideally it is desirable for the thermal conductivity provided by 130 to be less than that of air so that, for example, an embodiment may use such gases denoted below having thermal conductivity less than that of air. (e.g., carbon dioxide, argon, krypton, xenon, sulfur hexafluoride). Below is a table of thermal conductivities of some gases at 1 atmosphere, 298 degrees K:

| Compound | Thermal Conductivity (W/mK) |
|---|---|
| Helium | 0.147 |
| Hydrogen | 0.175 |
| Neon | 0.0483 |
| Nitrogen | 0.0255 |
| Oxygen | 0.0263 |
| air | 0.0259 |
| Carbon dioxide | 0.0169 |
| Argon | 0.0174 |
| Sulfur hexafluoride | 0.0121 |
| Krypton | 0.00943 |
| Xenon | 0.00565 |

In connection with the above-reference information for the gases, such information is generally available and known in the art. For example, data for all but Krypton, Xenon, and Sulfur hexafluoride (SF6), and air may be obtained from R C Reid, J M Prausnitz, B E Poling, *The Properties of Gases & Liquids,* 4th Edition, McGraw Hill, 1987. Data for Krypton, Xenon, and Sulfur hexafluoride (SF6), and air may be found, through publically available information in the internet, for example, using Wolfram Alpha™ computation knowledge engine Wolfram Alpha LLC available online at www.wolframalpha.com.

The jacket 120 used in an embodiment may generally be any suitable material that can withstand a vacuum and does not outgas. For example, the jacket 120 may be made from one or more of steel, copper, brass, aluminum or other metals. The column may have walls constructed of, for example, steel or titanium, but, more generally, may be made from any material that can withstand the high pressures and also be chemically inert to a mobile phase and sample utilized in an embodiment. As an alternative, an embodiment may select the column to have walls constructed from a material that does chemically interact with sample (e.g., ceramics will often interact with certain analytes), and coat/clad the interior wall of the column (e.g., which comes into contact with the sample and mobile phase in the fluidic path) with an inert material such as fused silica or PEEK. A preferred vacuum pressure that may be used is described above such as at pressures below $10^{-3}$ atm. The particle size used for the column material may have a size less than 2 microns, such as in the approximate inclusive range of 1.5-2 micron size particles. It should be noted that techniques herein may also be used with larger size particles but that thermal effects become less important for particles of larger sizes such as, for example, particles exceeding the general size range of 5-10 microns, or greater than 5 microns. Thus, thermal effects become more important for smaller sized particles. LC columns of any suitable dimension may be used in connection with techniques herein. Exemplary dimensions for LC columns that may be used in an embodiment may have a length of 20 mm to 300 mm, and a diameter which is approximately equal to or more than 100 µm to about 50 mm. As will be appreciated by those skilled in the art, thermal effects may be insignificant for small diameter columns, for example, approximately less than 100 µm, as heat transfer will minimize radial and axial gradients. At larger diameters, the size of about 50 mm may be based on practical limitations such as due to the pressure rating of the hardware. As diameter increases, it becomes significantly more expensive to make a tube that can withstand the necessary high pressures.

Figure 3:
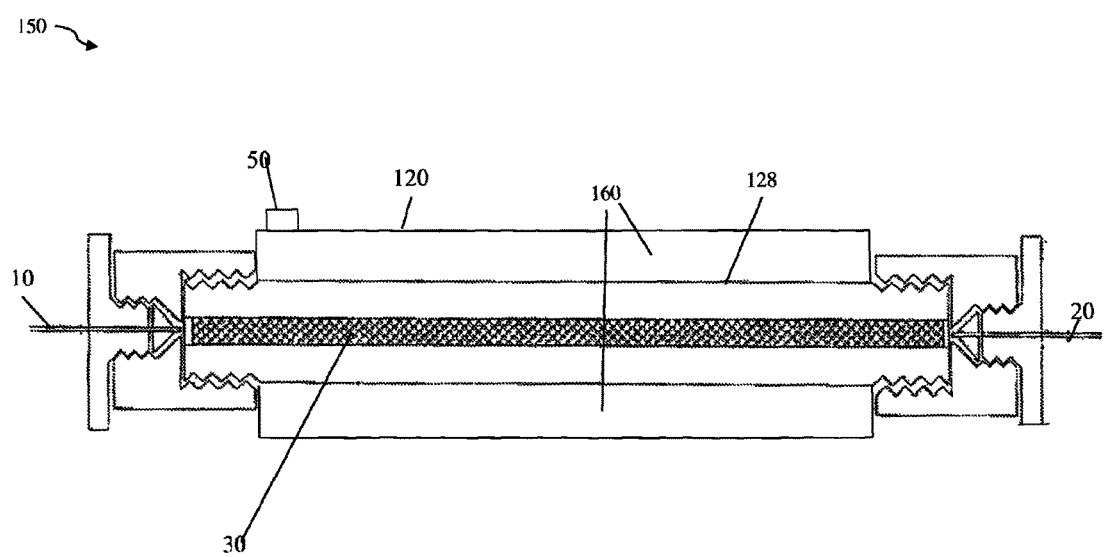

Referring to FIG. 3, shown is an example of another embodiment of a chromatography column in accordance with techniques herein. The embodiment of FIG. 3 may be used as the column 110 in the system of FIG. 1. FIG. 3 includes components similar to those of FIG. 2 with a difference that the insulation member or layer is denoted as 160 (rather than 130 as in FIG. 2) and is included as an integrated part or layer of the column. In the example 150, the column may be characterized as including a first inner portion 128 (the uninsulated column 128 as described above in connection with FIG. 2) surrounded by a second outer portion forming the insulating layer 160. In the example 150 of FIG. 3, the insulating layer 160 may not extend the entire length of the inner portion 128. The insulating layer 160 may be formed as described above in connection with element 130 of FIG. 2.

Figure 4:
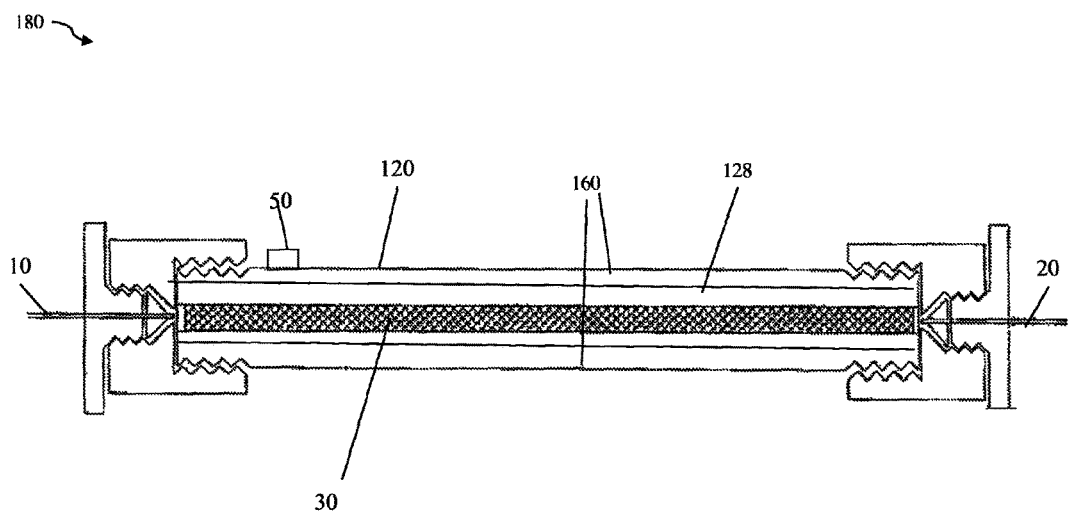

Referring to FIG. 4, shown is an example of another embodiment of a chromatography column in accordance with techniques herein. The embodiment of FIG. 4 may be used as the column 110 in the system of FIG. 1. FIG. 4 includes components similar to those of FIG. 3 where the insulation member or layer 160 is included as an integrated part or layer of the column. In the example 180 (as also in FIG. 3), the column may be characterized as including a first inner portion 128 (as described above in connection with FIG. 2) surrounded by a second outer portion forming the insulating layer 160. In the example 180 of FIG. 4, the insulating layer 160 may extend substantially the entire length of the inner portion 128. The insulating layer 160 may be formed as described above in connection with element 130 of FIG. 2.

When performing experiments using LC systems, it may be desirable to sometimes heat or increase the temperature of the mobile phase to be greater than ambient or air temperature. To this end, further exemplary embodiments are illustrated in connection with FIGS. 5A and 5B.

Figure 5A:
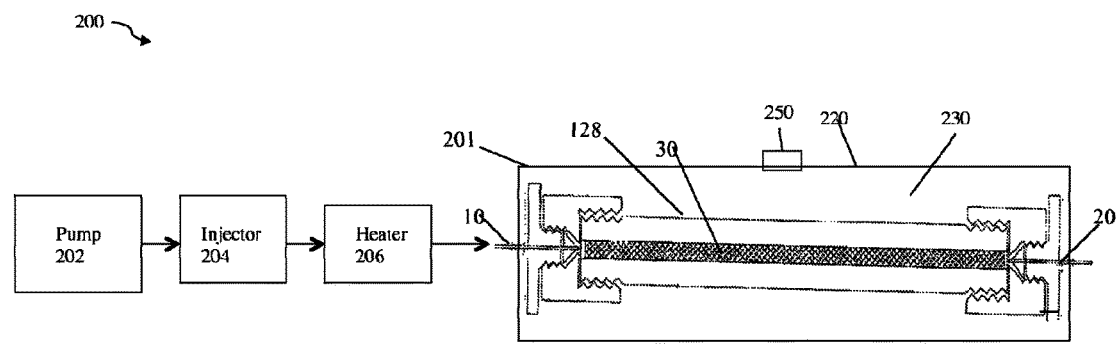
FIGS. 5A, 5B, 6 and 7 are examples of various chromatographic column embodiments and other components in accordance with techniques herein.
Figure 5B:
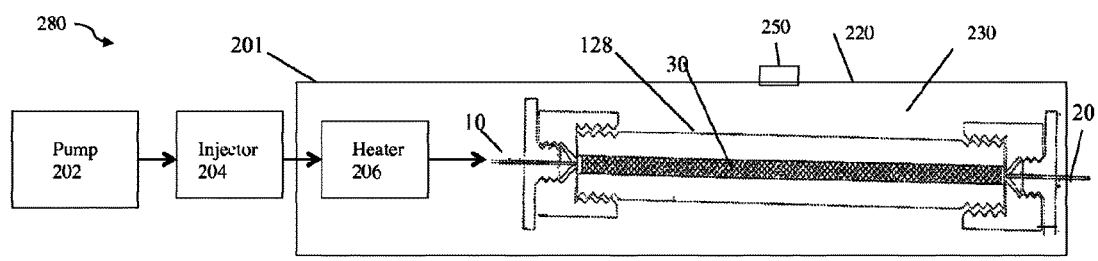

Referring to FIGS. 5A and 5B, shown are further example embodiments in which an active heating element may be positioned before the column to heat the mobile phase prior to the column inlet in accordance with techniques herein.

FIG. 5A illustrates an example 200 of components of the LC system. The example 200 includes a pump 202, injector 204, heater 206 and encasement or housing 201 enclosing the LC column in a manner similar to that as described above in connection with FIG. 2. The housing 201 may include through hole 250 having an exterior wall 220 functioning as the jacket 120 of FIG. 2. Element 230 may be the chamber forming the insulating layer as described above in connection with element 130 of FIG. 2. The heater 206 may be, for example, the ACQUITY Active Solvent heater provided by Waters Corporation. The heater 206 may, for example, be set at a desired set point temperature to heat the mobile phase having a flow path as represented by the arrows between the various components 202, 204, 206 and 201.

FIG. 5B is a further variation to that of FIG. 5A. The example 280 of FIG. 5B is similar to the example 200 of FIG. 5A with the difference that the heater 206 is included within the housing 201 in FIG. 5B.

It should be noted that element 201 may be, for example, a column heater compartment or oven into which the column is placed. The column heater may include appropriate airtight seals as described herein to which a vacuum pump may be connected (not shown) via through hole 250 as described above in connection with through hole 50 of FIG. 2. In such an arrangement, the column heater may apply additional heating, as may be needed, in addition to the active heating element represented by 206 for heating the mobile phase prior to entry into the column 128. Furthermore, an embodiment may use a column heater as described above in connection with FIG. 5A with or without use of the solvent heater 206. The column heater (such as represented by 201 in FIGS. 5A and 5B) may be, for example the Waters AQUITY UPLC® column heater.

In connection with the foregoing heater element 206 and/or embodiment where element 201 is a column heater, heating in connection with obtaining a desired set point may be performed using a feedback control (not illustrated) whereby the actual or observed temperature may be obtained, such as using one or more thermocouples, to provide feedback to electronic controls of the heating components (e.g., to increase/decrease amount of heat by controlling the heater based on whether the current temperature measured by the thermocouple is at the desired temperature set point, or within an acceptable threshold of such a set point). In an embodiment using the column heater, the column heater may be used to apply an additional source of heat to the column enclosed within 201 in an airtight manner. The additional source of heat provides for heating the column 128 via radiant heating from the surrounding environment. It should be noted that other suitable techniques may be used to also provide additional heat to the column 128 included within the housing 201 with the above-mentioned insulating member or layer 230 such as formed by the vacuum chamber between the outer wall of the column 128 and the wall 220 of the housing 201. For example, an optional heater or heating means may enclose or surround housing 201 which provides the ability to add radiant heat to compensate for potential non idealities in reaching true adiabatic conditions.

What will now be described are techniques that may be used in connection with performing an LC experiment during operation of an LC system to reduce the amount of time it takes to achieve steady state as described above with respect to measured axial thermal gradient whereby there will be substantially constant values for column inlet temperature $T_{in}$, column outlet temperature $T_{out}$ and the difference (e.g., within some accepted amount of measured threshold difference) between $T_{in}$ and $T_{out}$.

Techniques described in following paragraphs may use one or more independently controlled heaters in thermal contact with the column at various column positions. In some embodiments as described herein, a plurality of independently controlled heaters in thermal contact with the column at various column positions may be utilized. These independently controlled heaters may be used alone, or in combination with, other sources of heat that may be applied in connection with controlling the temperature of the column and liquid mobile phase passing therethrough.

Temperature is one parameter that may have a significant effect on the retention of an analyte. Temperature may alter, for example, the kinetics of adsorption and desorption between an analyte and the stationary phase or separation medium thereby affecting both the speed and selectivity of the separation. In performing LC experiments, it is important that the LC column achieve a steady state temperature in order to obtain reproducible results. Techniques described in following paragraphs provide for reducing the time needed to achieve such steady state with respect to column temperature. As described elsewhere herein, the steady state column temperature may be determined by having $T_{in}$ and $T_{out}$, and the difference therebetween (e.g., axial temperature gradient) be relatively or substantially constant.

Figure 6:
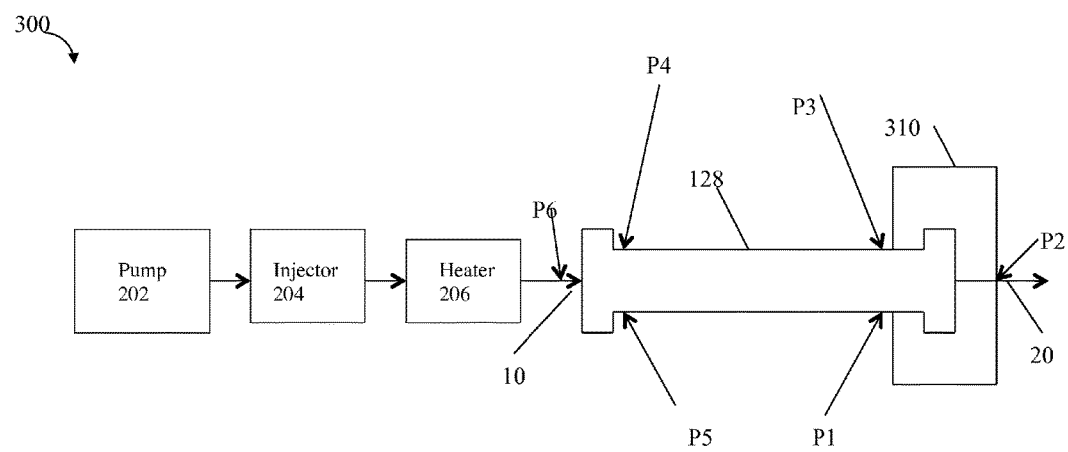

Referring to FIG. 6, shown is an example of an embodiment of components that may be used in connection with the techniques herein for reducing the amount of time required to achieve steady state as determined based on substantially constant measured values for $T_{in}$, $T_{out}$ and temperature difference between $T_{in}$ and $T_{out}$ (e.g., axial gradient that is substantially constant). The example 300 includes a pump 202, injector 204, heater 206, and uninsulated column 128 having inlet 10 and outlet 20 as described elsewhere herein. Additionally, the example 300 includes a heater 310 coupled to, and in thermal contact with, the column 128 at the column outlet 20. The column exit or outlet temperature $T_{out}$ may be measured, for example, by a thermocouple positioned at or near the column exit. Elements P1, P2 and P3 indicate exemplary positions where the thermocouple may be positioned to obtain the temperature measurement $T_{out}$. The heater 310 may be set, manually or through an automated control means (not illustrated), at a desired set point temperature. The observed actual temperature may be measured using the thermocouple and the heater 310 may be turned on/off or otherwise adjusted to increase or decrease an amount of heat from the heater 310 based on whether the measured temperature $T_{out}$ (e.g., such as from one of P1, P2 or P3) is at the desired set point value. As known in the art, a feedback technique such as using suitable electronic wiring, circuitry, and the like, may be used to automate control and operation of the heater 310. For example with reference back to FIG. 1, code executing on the computer 116 may provide a user interface by which a user may select and set a desired set point for $T_{out}$. The measured temperature $T_{out}$ may be provided to the computer system whereby code executing on the computer system may compare the measured $T_{out}$ to the desired set point value for $T_{out}$ and issue control signals to the heater 310 to appropriately control operation of the heater 310 in response to whether the measured $T_{out}$ is at the desired set point value for $T_{out}$.

$T_{in}$, the column inlet temperature as described above, may be measured in a manner similar to that as $T_{out}$. For example, a thermocouple may be used to measure $T_{in}$ at any suitable position at the column inlet such as represented by P4, P5 and P6. Based on the observed or measured values of $T_{in}$ and $T_{out}$ and determining a difference therebetween, an embodiment may determine when steady state has been reached as indicated by substantially constant measured values for $T_{in}$, $T_{out}$ and the axial thermal gradient or difference between $T_{in}$ and $T_{out}$.

The measurement of $T_{in}$ and $T_{out}$, control of the heater 310, and temperature set point selection for $T_{out}$ may be determined in using any suitable manual and/or automated technique as will be appreciated by those of ordinary skill in the art. For example, an embodiment may use automated techniques such as described above using control signals to control operation of the heater 310. Additionally, an embodiment may also determine the desired temperature set point for $T_{out}$ in an automated manner such as using an algorithm implemented by code executing on a processor that predicts the steady state column exit temperature based on a given $T_{in}$ and other parameters and uses this computed value of $T_{out}$ as the desired set point for $T_{out}$. The steady state column exit temperature may be determined algorithmically based on the particulars of an implementation. For example, a predicted steady state column exit temperature as a set point for $T_{out}$ may be determined based on/using, column dimensions (e.g., length and diameter), particle size, mobile phase composition (e.g., solvent), flow rate, column inlet temperature $T_{in}$, and thermal properties of the column assembly. For example, the following equation may be used in connection with automated techniques to automatically predict a desired $T_{out}$ (predicted column exit temperature) as a set point for steady state depending on the various parameters including a given $T_{in}$. For example, an embodiment may use a PID (proportional-integral-derivative) controller to drive the set temperature of $T_{out}$ to a steady state value based on a known or given $T_{in}$ and other system parameters. In this manner, such techniques may be used to determine and drive the system to steady state. As known in the art, a PID controller may be characterized as a generic control loop feedback mechanism (controller) as widely used in various type of control systems. The temperature increase in an adiabatic column that is heated via frictional heat can be predicted by the Equation:

$$\Delta T_L = (1 - \overline{\alpha T}) \frac{\Delta P}{\rho C_p} \qquad \text{EQUATION A}$$

where $\Delta T_L$ is the longitudinal temperature difference between column inlet and outlet (e.g., $T_{in}$-$T_{out}$), $\alpha$ is the thermal expansion coefficient of the mobile phase, $\overline{T}$ is the mean temperature of the mobile phase, $\Delta P$ is the pressure drop across the column, $C_p$ is the heat capacity of the mobile phase at constant pressure, and $\overline{\alpha T}$ represents the average of a quantity $\alpha T$, and $\rho$ is the density of the mobile phase. The value (1−$\alpha T$) is on the order of ⅔ (F Gritti and G Guiochon, Anal. Chem. 80 (2008) 5009). For example, using EQUATION A, an embodiment may use automated techniques to determine a predicted value for $T_{out}$ associated with steady state for a given or set $T_{in}$. Appropriate control signals may be sent to the heater/cooling unit 310 so that $T_{out}$ reaches and maintains (within some specified tolerance) its predicted steady state value. As different values for $T_{out}$ are desired based on different given values for $T_{in}$, such automated techniques may be used to determine and provide for adjusting $T_{out}$ (e.g., by controlling 310). More generally, EQUATION A may be used to determine particular pairs of values for $T_{in}$ and $T_{out}$ associated with a steady state. As described in more detail elsewhere herein, one or more heating and/or cooling units may be used to drive $T_{in}$ and/or $T_{out}$ to desired temperatures as determined using EQUATION A.

A method for calculating the predicted steady state column exit temperature based on the foregoing may be implemented, for example, using software executing on a processor such as of the computer 116 of FIG. 1. As described above, temperature control of the heater 310 may be obtained by adjusting or controlling the heater 310 via a feedback loop that monitors the column exit temperature and sends control signals to the heater 310 based on when a predicted desired set point for $T_{out}$ has been reached (e.g., when the measured column exit temperature $T_{out}$ is at or near (such as within a threshold amount of) the predicted value for $T_{out}$).

In connection with FIG. 6, it should be noted that the heater 206 may be optionally utilized so that an embodiment in accordance with techniques herein may only include heater 310 but not 206 as a solvent heater prior to entering the column 128. Additionally, in connection with FIG. 6, element 310 may be a heater or more generally a temperature control unit that provides heating and/or cooling.

As a variation to the embodiment of FIG. 6, the unit represented by 310 may be configured to be moveable or portable and readily positioned at other axial locations along the column 128 besides at the column exit or outlet as illustrated.

Figure 7:
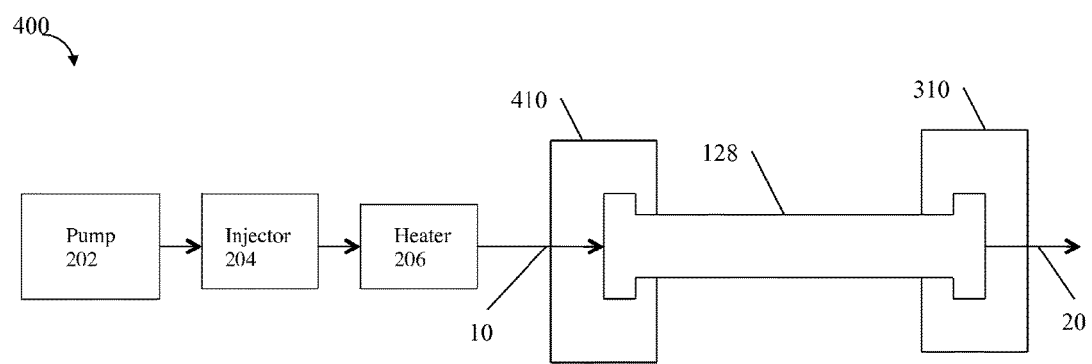

Referring to FIG. 7, shown is an example of another embodiment of components that may be used in connection with the techniques herein for reducing the amount of time required to achieve steady state as determined based on substantially constant values for $T_{in}$, $T_{out}$ and temperature difference between $T_{in}$ and $T_{out}$ (e.g., axial gradient that is substantially constant). The example 400 includes a pump 202, injector 204, heater 206, heater 310 and uninsulated column 128 having inlet 10 and outlet 20 as described above in connection with FIG. 6. Additionally, the example 400 includes a second heater 410 coupled to, and in thermal contact with, the column 128 at the column inlet 10. Element 410 may be similar to the heating and/or cooling unit represented by element 310 with the difference that 410 is located at the inlet of column 128 functioning to control $T_{in}$. Thus, in a manner similar to that as described above regarding $T_{out}$, $T_{in}$ may be set to a desired temperature set point and used as the set point for controlling heater 410. Heater 410 may be set, for example, via a manual and/or automated manner and the heater 410 may be controlled manually (e.g., user may turn on, off or otherwise adjust controls of the heater 410 based on observed $T_{in}$) or automatically (e.g., using a feedback technique with electronic temperature monitoring and control means to adjust the heater 410 based on observed or measured column inlet temperature $T_{in}$ and a desired set point $T_{in}$). Such temperature monitoring and control means may include use of a computer or processor having code executing thereon which obtains observed temperatures from temperature sensors (e.g., such as located at any of P1-P6 of FIG. 6), and determines appropriate control signals sent over electronic circuitry connected to appropriate ones of the heating/cooling or temperature control units to effect a desired temperature adjustment. The observed temperature(s) may be used to determine what control signals, if any, are sent to one or more of the temperature control unit(s) to achieve desired set point temperature(s) such as may be determined in accordance with EQUATION A.

Element 410 may be an independently controlled temperature control unit that provides heating and/or cooling. For example, $T_{in}$ may be selected as a desired set point and unit 410 may provide appropriate heating and/or cooling to achieve and maintain the desired set point for $T_{in}$. Using $T_{in}$ and the above-noted EQUATION A, a predicted desired set point for $T_{out}$ may be calculated and used as the desired set point for the unit 310. The units 310 and 410 may be independently controlled to achieve and maintain a different desired set point for each as may be used in an embodiment.

As another example of a use in connection with the embodiment 400 of FIG. 7 when performing an LC experiment, the heater 206 may not be utilized. Additionally, the unit 410 may have a desired temperature setting $T_{in}$ which is less than a desired temperature setting $T_{out}$ of unit 310. Unit 410 may function as a cooling unit to reduce temperature of the mobile phase to be less than ambient temperature and unit 310 may function as a heating unit to increase the temperature of the mobile phase to be greater than ambient temperature and also greater than $T_{in}$ (e.g., $T_{in}$<ambient temperature; $T_{out}$>ambient temperature, and $T_{in}$<$T_{out}$. As a further example, elements 410 and 310 may be cooling units having desired set points both of which are less than ambient temperature and also where the set point $T_{in}$ of 410 is less than the set point $T_{out}$ of 310 (e.g., $T_{in}$<ambient temperature; $T_{out}$<ambient temperature, and $T_{in}$<$T_{out}$). As yet a further example, elements 410 and 310 may be heating units having desired set points both of which are more than ambient temperature and also where the set point $T_{in}$ of 410 is less than the set point $T_{out}$ of 310 (e.g., $T_{in}$>ambient temperature; $T_{out}$>ambient temperature, and $T_{in}$<$T_{out}$).

More generally, an embodiment in accordance with techniques herein may include a plurality of heating and/or cooling units such as denoted by 310, 410 above at any location along the column axis in thermal contact with the column 128.

As will be appreciated by those skilled in the art and in connection with various examples described herein, EQUATION A may be used to determine and predict a desired steady state value for $T_{out}$ given a particular set of parameters including $T_{in}$. A heating/cooling unit 310 may then be controlled to provide for appropriately adjusting $T_{out}$ to be at a desired steady state predicted set point temperature based on EQUATION A. In a similar manner such as described in connection with FIG. 7, such techniques may be used to control operation of 410 thereby driving or adjusting $T_{in}$ to a desired predicted value such as based on a particular given $T_{out}$ value. More generally, the $\Delta T_L$ of EQUATION A represents the temperature difference between two temperatures in connection with steady state. As such, given EQUATION A and one of the two temperatures used to compute $\Delta T_L$, the second of the two temperatures may be predicted. As described above, $\Delta T_L$, the temperature difference, may be between $T_{in}$ and $T_{out}$ where either one may be known which is then used with EQUATION A to determine via calculation the second temperature (e.g., $T_{in}$ fixed or known and use EQUATION A to drive or determine $T_{out}$. Alternatively, $T_{out}$ may be fixed or known and may be used to with EQUATION A to determine a predicted $T_{in}$). More generally, the automated techniques and EQUATION A may be used with any two temperatures used to determine $\Delta T_L$ where one of the two temperatures may be given and used to predict the other second temperature in connection with achieving a desired steady state. An embodiment may control operation of 310 and/or 410 based on desired temperatures for experimentation.

Figure 8:
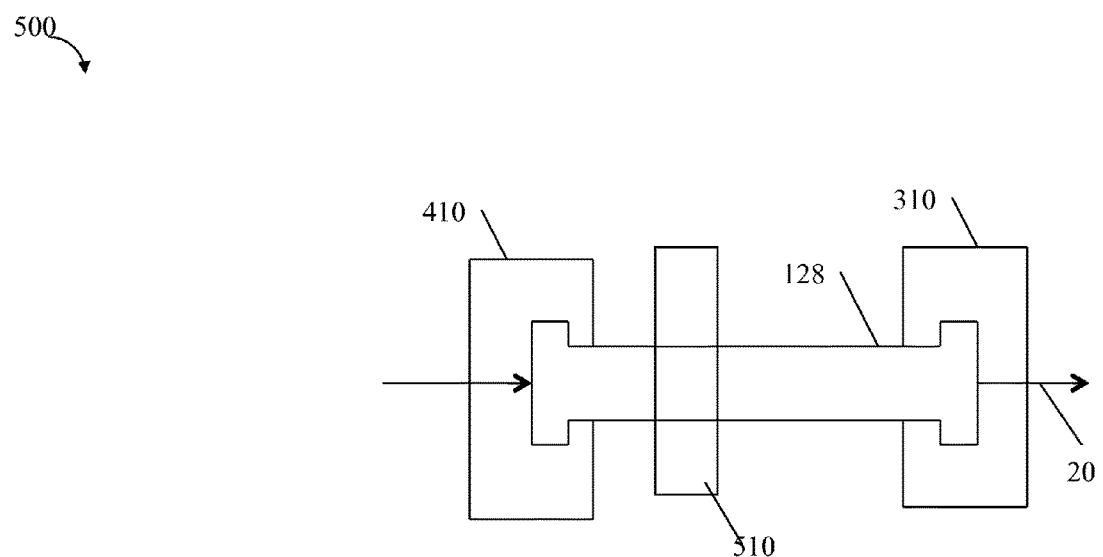

FIG. 8 is another example of such an embodiment. In the example 500, the components similarly numbered may be as described above in connection with FIG. 7. Additionally, a third unit 510 providing heating and/or cooling may be positioned along the axis of column 128 in thermal contact with the column 128. The units 310, 410 and/or 510 may be secured, coupled to, or more generally in thermal contact with, the column 128. In one embodiment, the units 310, 410 and/or 510 may be attached or secured to the column 128 using clamps or other suitable means. For example, in one embodiment, ends of the column 128 may be positioned within units represented by elements 310 and 410.

Based on the axial position or location on column 128 from the column inlet, element 510 may be considered as a unit for heating and/or cooling in a manner similar to 310 and/or 410. More generally, depending on the axial location or position of 510 along the column, the desired set point for 510 may be determined in accordance with EQUATION A. The temperature, $T_{intermediate}$, at or near location 510 may be measured using temperature sensing devices as described herein in connection with measuring an observed value for $T_{in}$ and/or $T_{out}$. Similar means may also be used to control and adjust heating/cooling unit 510 as described for 310 and/or 410. A set point for $T_{intermediate}$ may be determined, for example, based on a proportional temperature difference between $T_{in}$ and $T_{out}$ where such proportion is based on the distance or location of $T_{intermediate}$ with respect to locations in the axial direction along 128 of $T_{in}$ and $T_{out}$. For example, if 510 $T_{intermediate}$ is located midway or midpoint between $T_{in}$ and $T_{out}$ along 128, $T_{intermediate}$ may be determined as approximately $T_{in}+(\frac{1}{2}\Delta T_L)$ (e.g., also may be represented as $(T_{in}+T_{out}/2)$. Thus, the desired set point temperature for $T_{intermediate}$ may be estimated as a value between $T_{in}$ and $T_{out}$ which is proportional to the location or distance of $T_{intermediate}$ between the axial locations along column 128 where $T_{in}$ and $T_{out}$ are measured (e.g., column inlet and outlet).

The desired target or set point temperature of 510 may vary proportionally with the axial location of 510 on the column 128. Element 510 may be associated with an intermediate temperature, $T_{intermediate}$, and may be used in a manner similar to that as described herein with $T_{in}$ and/or $T_{out}$. For example, any one or more of 310, 410 and/or 510 may be adjusted in accordance with EQUATION A to achieve steady state. For example, $T_{in}$ may be known or given (whereby 410 may not be used or operated) and units 510 and/or 310 may be controlled to achieve desired set point temperatures based on EQUATION A. $T_{out}$ may be known or given (whereby 310 may not be used or operated) and units 510 and/or 410 may be controlled to achieve desired set point temperatures based on EQUATION A. As another example, in connection with conditions for a particular experiment, set point values for $T_{in}$, $T_{out}$ and $T_{intermediate}$ may be determined based on EQUATION A and units 410, 510 and/or 310 accordingly operated to achieve the desired set points values. Based on the above, an intermediate point $T_{intermediate}$ may be located on the chromatography column between the inlet and the outlet. The intermediate point of the chromatography column may be set to an intermediate temperature using unit 510 (e.g. prior to injecting a sample in connection with obtaining steady state). The intermediate temperature at the intermediate point may be between desired set point values for $T_{in}$ and $T_{out}$ (such as determined using EQUATION A). In one aspect, the desired intermediate temperature set point may be determined as a sum of $T_{in}$ and an approximated value where the approximated value is a temperature offset proportional to a distance of the intermediate point from the column inlet. In a similar manner, the desired intermediate temperature set point may be determined as a temperature offset with respect to $T_{out}$. This temperature offset may be an approximated value proportional to a distance of the intermediate point from the outlet.

Thus, the example 500 of FIG. 8 illustrates one possible implementation of techniques herein using a plurality of units providing heating and/or cooling. By adding thermal energy (or otherwise more generally using one or more auxiliary heating and/or cooling units as described herein) to various axial location points along a chromatographic column, thermal equilibrium may be obtained in less time than if the column were allowed to heat naturally via friction and other artifacts of the experiment providing heat without use of the additional units such as 210, 310, 410, and/or 510.

It should be noted that each of the exemplary embodiments of FIGS. 6, 7, and 8 as well as other embodiments such as described above (e.g., with additional heaters in thermal contact with the column and/or placement of heaters in different axial positions along the column) may include an insulating jacket surrounding the column and heaters.

As described above with reference again to FIG. 8, an embodiment may use elements 410, 510 and 310 in connection with, respectively, $T_{in}$, $T_{intermediate}$, and $T_{out}$. As a variation to this, an embodiment may, for example, omit use of $T_{out}$ and 310 and rather include and use only 410 and 510 respectively with $T_{in}$ and $T_{intermediate}$ in connection with techniques herein. As yet another variation, an embodiment may, for example, omit use of $T_{in}$ and 410 and rather include and use only 510 and 310 respectively, with $T_{intermediate}$ and $T_{out}$ in connection with techniques herein.

As yet another variation, rather than have 510 represent a heating/cooling unit which may be controlled or adjusted, an embodiment may alternatively just measure or monitor one or more intermediate temperatures at one or more points between $T_{in}$ and $T_{out}$ along column 128 as part of feedback control processing. However, in this case, the one or more intermediate temperatures measured may be used to modulate or control the units 410 and/or 310 based on a measured intermediate temperature. The intermediate temperature(s) may be used as the monitored or observed temperatures in connection with feedback techniques rather than use of measured or observed values for $T_{in}$ and/or $T_{out}$ at respective column endpoints. In this manner, an intermediate temperature may be used as a monitored or observed temperature to adjust $T_{in}$ and/or $T_{out}$ by controlling operation of 410 and/or 310 until the intermediate temperature observed is about at its desired set point value (obtained through adjustments made using units 410 and/or 310). To further illustrate, an embodiment may measure $T_{intermediate}$ to determine whether the measured $Ti_{ntemediate}$ is at a desired value or set point. Accordingly, adjustments may be made to unit 410 until the measured $T_{intermediate}$ is at its desired set point. Thus, $T_{intermediate}$ may be used to control or adjust 410 rather than make such adjustments to 410 based on a temperature measured at $T_{in}$ (endpoint of 128 at or near the location of 410 such as illustrated in FIG. 6).

Figure 9:
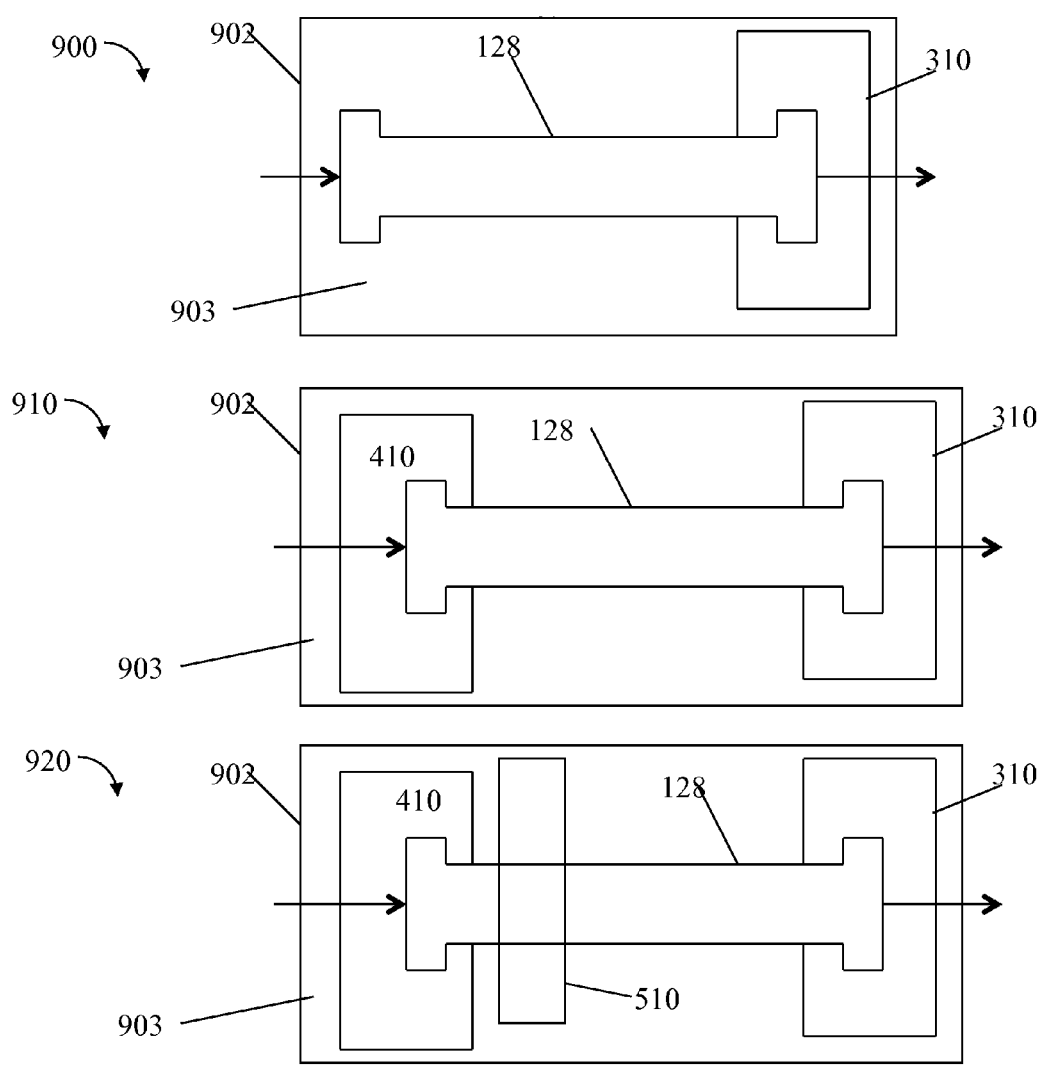

Referring to FIG. 9, shown are examples of the embodiments from FIGS. 6, 7 and 8 with the addition of a thermally insulating layer. Element 902 may represent a thermally insulating jacket in each of 900, 910 and 920. The example 900 is an illustration of the column embodiment of FIG. 6 in the surrounding jacket 902. The example 910 is an illustration of the column embodiment of FIG. 7 in the surrounding jacket 902. The example 920 is an illustration of the column embodiment of FIG. 6 in the surrounding jacket 902. The jacket 902 may provide thermal insulation by reducing heat loss due to convective air currents. In one embodiment, the jacket 902 may provide sufficient insulation preventing thermal conductivity between the column (and its contents) and ambient temperature such as of the environment outside of or surrounding the jacket 902.

The jacket 902 may be made from polystyrene foam (Styrofoam®), or more generally, any material exhibiting low thermal conductivity to act as an insulating member. Polymers such as polymethacrylate, silicone, urethane, polyolefins, polyamide, polysulfone, polyethyramide, polycarbonate, rubber, polyester, polyfluoroelastomers and polyethylene terephthalate, and the like, may also be used to form the jacket 902. Additionally, ceramics E.g., such as aerogels), fibrous materials (e.g., such as methylcellulose and fiberglass) and the like, may also be used to form the jacket 902. Although various thermal insulating materials have been set forth in the foregoing illustrative embodiments as to materials that may be used to form jacket 902, any various suitable thermally insulting materials known in the art may be utilized. It will be appreciated that such materials may be so shaped as to insulate the area around the chromatography column to create a controlled air space or chamber so as to prevent or minimize a radial thermal gradient within the column. Furthermore, although such materials may be illustrated as immediately surrounding the column, such materials may also be integrated into the column itself, for example, such as used to form the column outer walls.

As another variation, the jacket 902 may be made of steel or metal as described above in connection with FIG. 2 so that the insulating layer or member is not the jacket 902 itself but rather the airspace 903 surrounding the uninsulated column 128 (e.g., between the column 128 and the surrounding jacket 902). In this case, element 903 may be the chamber or space, such as the vacuum chamber, forming the insulating layer and may be formed using any of the techniques, gases (e.g., insert gas, atmospheric gas), and the like, as described elsewhere herein such as in connection with FIG. 2. In one embodiment, the chamber or airspace 903 between the column 128 and the jacket 902 (e.g., surrounding the column 128) may be at ambient pressure and aerogel particles may be included in the area 903 to provide insulation. Alternatively, the airspace 903 including the aerogel particular may be form a vacuum chamber having a pressure less than ambient pressure. Examples of such pressures are described elsewhere herein. As a variation to the area 903 including aerogel particles, the column 128 may be placed in a molded aerogel component. The molded aerogel may surround the column and may be formed, for example, from two separately molded halves or portions which, when placed together, form a desired cavity approximating the shape of the column. The foregoing two molded aerogel portions may be fitted together as part of assembly with the column inserted into the formed cavity. The foregoing embodiments using molded aerogel or aerogel particles in a chamber may be used as an means of insulation in connection with any of the embodiments of the column described herein such as, for example, using one or more additional heating/cooling units.

Figure 10:
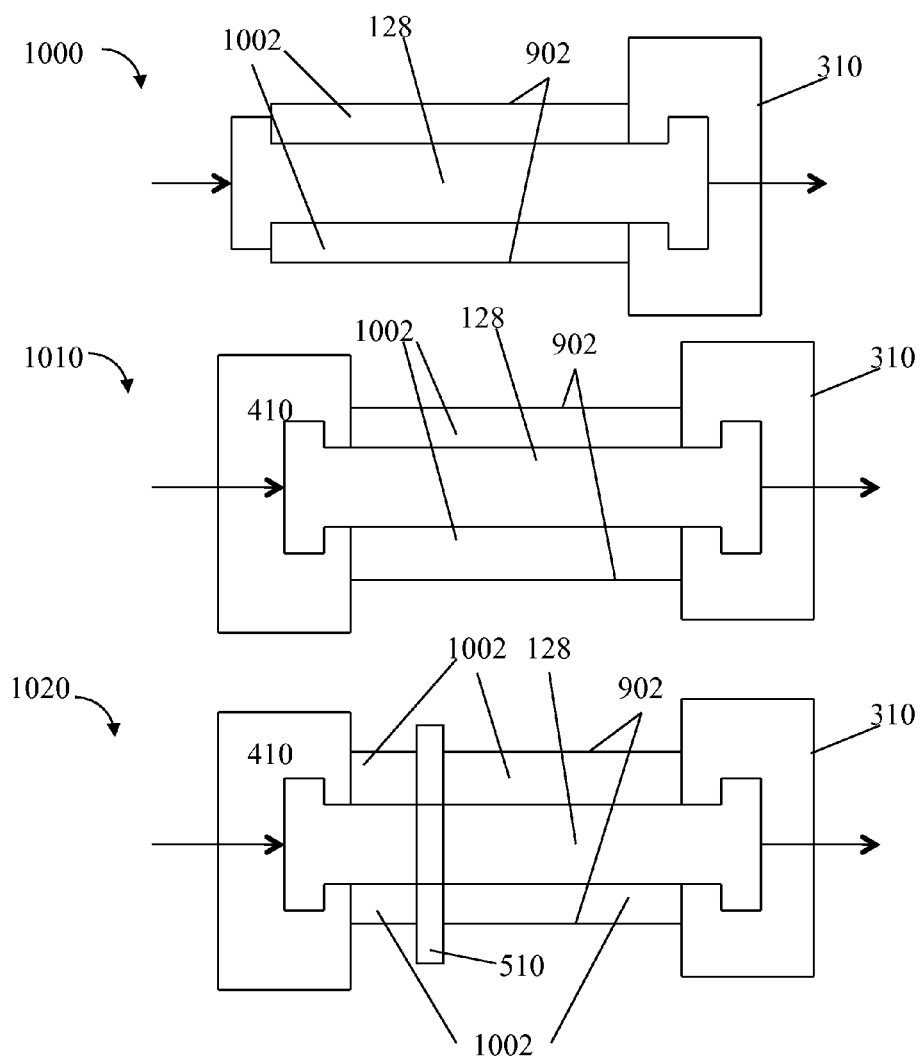

Referring to FIG. 10, shown are examples of the embodiments from FIGS. 6, 7 and 8 with the addition of a thermally insulating layer 1002. In the examples 1000, 1010 and 1020 of FIG. 10, the insulating layer 1002 may be an integral component of the column 128 such as described elsewhere herein in connection with FIGS. 3 and 4. In the examples 1000, 1010 and 1020, the insulating layer 1002 may be formed from any of the materials of the jacket 902 as described above. As a further variation, the insulating layer 1002 may be formed as a layer between a surrounding outer jacket 902 forming the outer walls of the combination of the column 128 and insulating layer 1002. The jacket 902 in this case may be made of steel, titanium, or other suitable material such as described elsewhere herein in connection with FIG. 2 and the insulating layer 1002 may be the chamber or space, such as the vacuum chamber, forming the insulating layer using any of the techniques, gases (e.g., insert gas, atmospheric gas), and the like, as described elsewhere herein such as in connection with FIG. 2 (and above in FIG. 9).

In connection with the example 1020, it should be noted that the unit 510 that performs heating and/or cooling should have sufficient thermal contact with the uninsulated column 128. For example, the insulating layer 1002 is illustrated as being formed around the unit 510 in areas bounded by or between, for example, units 410 and 510 and bounded by, or between, units 510 and 310.

In connection with embodiments described herein, such as with FIGS. 9 and 10, utilizing an insulating layer and/or jacket, it will be appreciated by those of ordinary skill in the art that the column inlet temperature, $T_{in}$ and column outlet temperature, $T_{out}$, may be measured by placement of various thermocouples in thermal contact with the uninsulated column 128 such as between any insulating layer and the column 128.

Axial control of column temperature as may be achieved using embodiments described herein such as in connection with FIGS. 6-10 may provide additional benefits. For example, axial control of temperature such as by control and selection of $T_{in}$ and $T_{out}$ may facilitate reproducibility of experimental conditions and chromatographic methods. Such techniques may provide for reproducibility of experimental conditions using columns having similar properties as well as different properties. For example, a typical HPLC column with a mean particle size of 5 microns generates less heat than a column of equivalent dimensions using 1.7 micron size particles. Without use of the techniques herein, the resulting thermal gradient during experiments may be different on the two columns resulting in differences in experimental data obtained using the two columns. The techniques herein may be used with the two columns—each using a different size particle—to create identical thermal gradients for the two columns.

As another example, one way to increase throughput in chromatography is to operate at a faster flow rate. It may not be desired or expected to have an increased flow rate affect chromatographic selectivity. However, the thermal gradients across two columns would not be identical where the two columns have the same properties (e.g., dimensions, particle size, etc. affecting the experiment) and where each of the two columns has a different flow rate (e.g., since the frictional heat generated varies with, and is directly proportional to, the flow rate of the mobile phase). In experiments where the chromatographic selectivity (e.g., distance between peaks of eluting analytes) is altered with the changing flow rate, the axial thermal gradient may be altered so that the two experiments using the different flow rates provide similar selectivity. As known in the art, chromatographic selectivity (also referred to as a separation factor or relative retention ratio) is a measure of the time or distance between the maxima of two peaks. The chromatographic selectivity may be represented as K2/K1 where K1 is the retention factor of the first peak and K2 is the retention factor of the second peak. If K2/K1=1 then the peaks have the same retention and co-elute.

As another advantage, adding one or more independently controlled heaters along the column body such as described above may reduce overall costs when compared to other alternatives such as use of a column heater.

In connection with embodiments as described herein such as using a vacuum insulating layer or chamber surrounding the LC column, true adiabatic conditions may be approached to minimize radial thermal gradients and eliminate or minimize convective heat loss.

In connection with techniques herein, the inventors performed experiments that will now be described. A 2.1×100 mm Waters ACQUITY BEH C18 1.7 µm column was connected to a Waters ACQUITY™ UPLC instrument. 0.5 microliters of a sample containing the following 5 components: (1) 0.046 mg/mL thiourea; (2) 0.080 mg/mL dodecanophenone; (3) 0.1 mg/mL tetradecanophenone; (4) 0.1 mg/mL hexadecanophenone; and (5) 0.483 mg/mL di-n-decyl phthalate, was injected onto the column using a mobile phase of acetonitrile. Analyses were made using the following flow rates: 0.45, 0.50, 0.55, 0.65, 0.75, 0.85, 0.95, 1.05, 1.10, 1.15, and 1.20 mL/minute. The column was thermally equilibrated between changes in flow rate by monitoring repeat injections of the test probes until retention time reproducibility was achieved. Detection was by UV at 240 nm.

The vacuum system used in the experiment was a Pfeiffer Vacuum TSH 071E Turbomolecular Drag Pumping Station, which included the following standard components: a Pfieffer-Balzers TMH-071P Turbomolecular Drag Pump, with DN-63-ISO inlet flange and comes standard with a solid-state frequency converter, and electronic controls. A dual-stage, high-performance rotary vane pump with a pumping speed of 2.5 m$^3$/h from Pfeiffer (Duo 2.5 model PKD41707) was used to bring the vacuum quickly to ~10$^{-2}$ torr before starting the turbo pump. The vacuum chamber for the column and the connections to the vacuum system were constructed from MDC Vacuum Products (Hayward, Calif.) 304 stainless steel tubing and seals (Viton® or Buna-N® O-rings) rated to 10$^{-8}$ torr. For vacuum reading between atmosphere to 10$^{-2}$ mbar/Torr an Edwards active pirani gauge part number D02177000 APG-1-NW16 ST/ST was used. For vacuum readings between 10$^{-3}$ to 10$^{-8}$ mbar/Torr an Edwards active Inverted Magnetron Gauge part number D14641000 AIM-S-NW25 was used. The vacuum readings were taken as close (~4" away) from the column vacuum chamber.

Chromatographic performance was evaluated for columns under four different environments: (A) Isothermal: The column was placed in a re-circulating water bath (RTE-111, Thermo NESLAB) maintained at 25C; (B) Still air: The column was placed inside a box of approximately 20"×33"×34" to minimize convection in the surrounding air; (C) Insulated with aerogel: Column was placed inside a chamber filled with granular aerogel from United Nuclear Scientific (Laingsburg, Mich.); (D) The column was jacketed in a vacuum of 3×10$^{-5}$ torr using a roughing pump and a diffusion pump.

Figure 11:
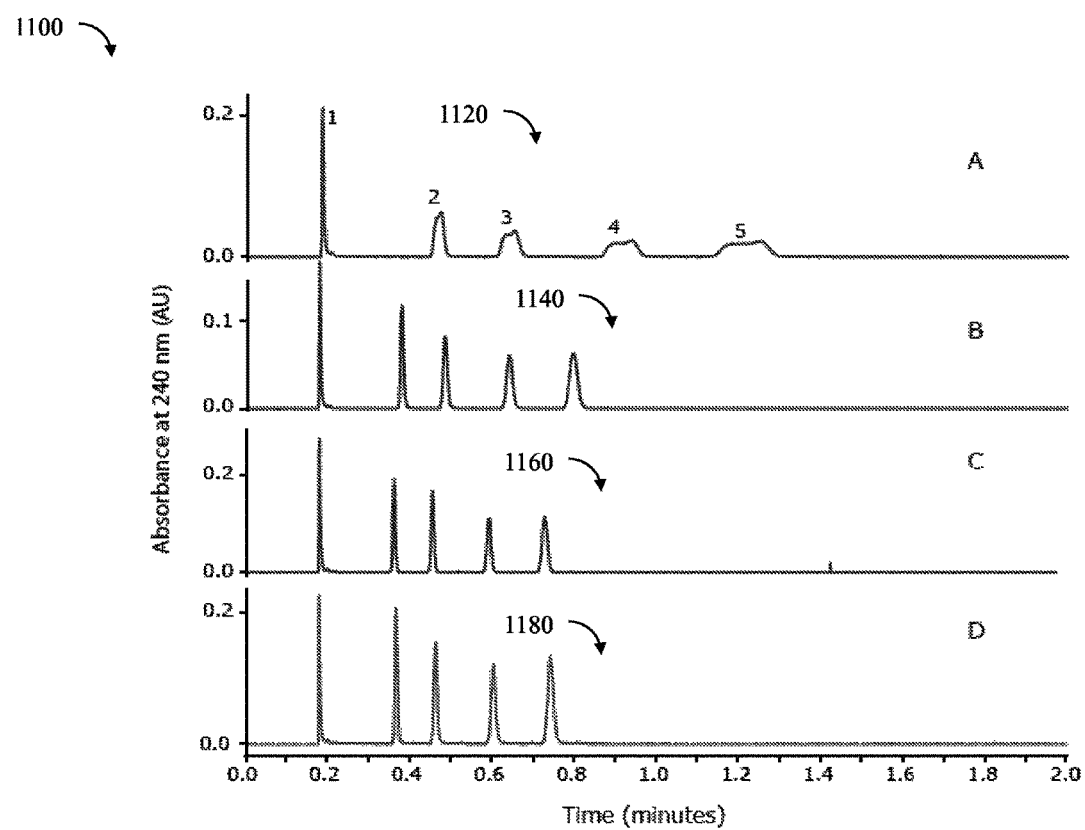
FIG. 11 is an example illustrating chromatograms from test results performed by the inventors in accordance with testing different environments.

Referring to FIG. 11, shown are chromatogram of the resulting separations for the above-mentioned four testing environments (A)-(D). The example 1100 includes 4 sets of chromatographic data obtained for a flow rate of 1.2 mL/minute. Element 1120 represents the chromatogram obtained for testing environment condition (A) for isothermal conditions where the column was placed in a re-circulating water bath (RTE-111, Thermo NESLAB) maintained at 25 C. Element 1140 represents the chromatogram obtained for testing environment condition (B) using still air where the column was placed inside a box of approximately 20"×33"×34" to minimize convection in the surrounding air. Element 1160 represents the chromatogram obtained for testing environment condition (C) where insulation was provided using aerogel where, as noted above, the column was placed inside a chamber filled with granular aerogel from United Nuclear Scientific (Laingsburg, Mich.). Element 1180 represents the chromatogram obtained for testing environment condition (D) whereby the column was jacketed in a vacuum of 3×10$^{-5}$ torr using a roughing pump and a diffusion pump. In connection with the chromatograms of 1100, the X axis of each denotes time, in minutes. In this example, the detector was a UV absorbance detector so that the detection units on the Y axis represent absorbance at 240 nm (AU). Each of the chromatograms 1120, 1140, 1160 and 1180 includes 5 peaks denoted 1-5 which respectively correspond to peaks for the 5 components of the sample as described above.

Shown below is a table illustrating the plate count for Peak (4) corresponding to hexanophenone, at the different flow rates. Results show that as flow rate increases, the plate count is highest in the cases where the column is at near adiabatic conditions.

| Flow Rate (mL/min) | (A) Isothermal | (B) Still air | (C) Insulated | (D) Vacuum |
|---|---|---|---|---|
| 0.45 | 25,536 | 25,045 | 27,160 | 27,227 |
| 0.50 | 22,598 | 22,829 | 26,108 | 26,892 |
| 0.55 | 19,175 | 20,908 | 24,956 | 26,382 |
| 0.65 | 12,733 | 16,954 | 22,756 | 25,518 |
| 0.75 | 7,997 | 13,492 | 20,747 | 23,607 |
| 0.85 | 5,099 | 10,866 | 19,014 | 22,104 |
| 0.95 | 3,389 | 8,926 | 17,386 | 20,489 |
| 1.05 | 2,357 | 7,386 | 15,875 | 18,898 |
| 1.15 | 1,715 | 6,259 | 14,567 | 17,098 |
| 1.20 | 1,478 | 5,839 | 14,095 | 16,371 |

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. An apparatus for performing liquid chromatography comprising:
   a liquid chromatography column;
   a jacket surrounding an entirety of the liquid chromatography column; and
   an insulating member surrounding the entirety of the liquid chromatography column, the insulating member comprising a vacuum chamber having the entirety of the liquid chromatography column arranged therein, the vacuum chamber formed in an area between the entirety of the liquid chromatography column and the jacket,
   wherein the vacuum chamber comprises a gas, the gas comprising one of an inert gas or a heavy gas, wherein the inert gas or the heavy gas is at a pressure of about 10$^{-3}$ atm or less and a thermal conductivity of the inert or heavy gas within the vacuum chamber is about or less than 0.02 W/mK.

2. The apparatus of claim 1, wherein the inert gas is any of argon, krypton, xenon, carbon dioxide and sulfur hexafluoride.

3. The apparatus of claim 1, wherein the liquid chromatography column and the insulating member are integrated into a single component forming an insulated liquid chromatography column.

4. The apparatus of claim 1, wherein the jacket is an outer layer of a housing of a column heater.

5. The apparatus of claim 1, wherein the insulating member substantially prevents a radial thermal gradient from forming within the liquid chromatography column.

6. The apparatus of claim 1, further comprising a heater that heats a mobile phase prior to an inlet of the liquid chromatography column.

7. The apparatus of claim 6, wherein the heater and the liquid chromatography column are included in a column heater and the vacuum chamber is formed in an area between the liquid chromatography column and an outer wall of the column heater.

8. An apparatus for performing liquid chromatography, comprising:

a chromatography column; and an insulating member surrounding the chromatography column wherein the insulating member is formed from a vacuum chamber surrounding the chromatography column, the vacuum chamber comprising a heavy gas, wherein the heavy gas is at a pressure of about $10^{-3}$ atm or less and a thermal conductivity of the heavy gas within the vacuum chamber is about or less than 0.02 W/mK.

9. The apparatus of claim 8, the heavy gas comprising at least one of krypton, xenon, and sulfur hexafluoride.

10. The apparatus of claim 8, the heavy gas comprising sulfur hexafluoride.

11. A liquid chromatography system, comprising:

a chromatography column; and an insulating member comprising a vacuum chamber surrounding at least a portion of the chromatography column, the insulating member configured to cause a formation of a substantially adiabatic condition in the chromatography column during operation of the liquid chromatography system, the vacuum chamber comprising a heavy gas, wherein the heavy gas is at a pressure of about $10^{-3}$ atm or less and a thermal conductivity of the heavy gas within the vacuum chamber is about or less than 0.02 W/mK.

12. The liquid chromatography system of claim 11, the substantially adiabatic condition formed without an application of heating to the chromatography column.

13. The liquid chromatography system of claim 11, the substantially adiabatic condition formed without an application of cooling to the chromatography column.

14. The liquid chromatography system of claim 11, the insulating member configured to substantially prevent a formation of a radial thermal gradient in the chromatography column during operation of the liquid chromatography system.

15. The liquid chromatography system of claim 14, the insulating member configured to substantially prevent the formation of the radial thermal gradient without an application of heating or cooling to the chromatography column.

16. The liquid chromatography system of claim 11, the insulating member configured to cause a formation of a substantially steady state temperature in the chromatography column during operation of the liquid chromatography system.

17. The liquid chromatography system of claim 16, the insulating member configured to cause the formation of the substantially steady state temperature in the chromatography column without an application of heating or cooling to the chromatography column.

18. The liquid chromatography system of claim 16, the steady state comprising a $T_{in}$ of a mobile phase entering the chromatography column, a $T_{out}$ of the mobile phase exiting the chromatography column, and an axial thermal gradient of the mobile phase being substantially constant.

19. The liquid chromatography system of claim 11, the heavy gas comprising at least one of krypton, xenon, and sulfur hexafluoride.

20. The liquid chromatography system of claim 11, the heavy gas comprising sulfur hexafluoride.

* * * * *